US009936862B2

(12) United States Patent
Kennedy

(10) Patent No.: US 9,936,862 B2
(45) Date of Patent: Apr. 10, 2018

(54) VIDEO RECORDING AND IMAGE CAPTURE DEVICE

(75) Inventor: Bruce L. Kennedy, Santa Barbara, CA (US)

(73) Assignee: Karl Storz Imaging, Inc., Goleta, CA (US)

(*) Notice: Subject to any disclaimer, the term of this patent is extended or adjusted under 35 U.S.C. 154(b) by 1927 days.

(21) Appl. No.: 10/662,599

(22) Filed: Sep. 15, 2003

(65) Prior Publication Data
US 2004/0133072 A1 Jul. 8, 2004

Related U.S. Application Data

(60) Provisional application No. 60/410,456, filed on Sep. 13, 2002.

(51) Int. Cl.
A61B 1/04 (2006.01)
A61B 1/00 (2006.01)
(Continued)

(52) U.S. Cl.
CPC ............ A61B 1/042 (2013.01); A61B 1/0005 (2013.01); A61B 1/00022 (2013.01); A61B 1/00039 (2013.01); A61B 1/00041 (2013.01); A61B 1/00045 (2013.01); H04N 7/183 (2013.01); H04N 9/8042 (2013.01); H04N 5/765 (2013.01); H04N 5/77 (2013.01); H04N 5/775 (2013.01); H04N 5/781 (2013.01); H04N 5/85 (2013.01)

(58) Field of Classification Search
CPC ........... A61B 9/26; A61B 9/28; A61B 9/5212; A61B 2017/00203; A61B 2017/00207; A61B 2017/00212; A61B 2017/00225

USPC ............... 600/102, 118, 146, 109, 132, 160; 248/917–924; 312/223.2; 345/905; 348/65, 794, 836, 838–839
See application file for complete search history.

(56) References Cited

U.S. PATENT DOCUMENTS 4,625,714 A 12/1986 Toyota et al.
5,045,955 A 9/1991 Ikeda
(Continued)

FOREIGN PATENT DOCUMENTS

DE 4336526 5/1994
JP 1147085 A 6/1989
(Continued)

OTHER PUBLICATIONS

Translation of the Japanese Office Action, Application No. 2004-536547, dated Oct. 28, 2008, 5 pages.

Primary Examiner — Anhtuan T Nguyen
Assistant Examiner — William Chou
(74) Attorney, Agent, or Firm — Whitmyer IP Group LLC

(57) ABSTRACT

A video recording and image capture device for documenting surgical procedures that includes a main board for executing a plurality of software, a multimedia interface operable to receive a video signal and process it into an MPEG layer stream, the video interface connected on a first bus to the main board, a hard drive to record an MPEG layer stream as a file, an optical media drive to write an MPEG layer stream as a file, the hard drive and the optical media drive operably connected on a second bus, the bus being vertically stacked and connected to the main board, and a touchscreen interactive for user control, connected to the main board on a second bus to control the video interface.

18 Claims, 17 Drawing Sheets

(51) Int. Cl.
*H04N 7/18* (2006.01)
*H04N 9/804* (2006.01)
*H04N 5/765* (2006.01)
*H04N 5/77* (2006.01)
*H04N 5/775* (2006.01)
*H04N 5/781* (2006.01)
*H04N 5/85* (2006.01)

(56) References Cited

U.S. PATENT DOCUMENTS

| | | | |
|---|---|---|---|
| 5,235,510 A * | 8/1993 | Yamada et al. | 600/300 |
| 5,740,801 A * | 4/1998 | Branson | 600/407 |
| 5,894,322 A | 4/1999 | Hamano et al. | |
| 6,016,439 A | 1/2000 | Acker | |
| 6,067,075 A | 5/2000 | Pelanek | |
| 6,120,435 A * | 9/2000 | Eino | 600/118 |
| 6,144,549 A * | 11/2000 | Moss et al. | 361/679.22 |
| 6,146,523 A * | 11/2000 | Kenley et al. | 210/143 |
| 6,184,922 B1 | 2/2001 | Saito et al. | |
| 6,224,542 B1 | 5/2001 | Chang et al. | |
| 6,272,470 B1 | 8/2001 | Teshima | |
| 6,278,444 B1 * | 8/2001 | Wilson et al. | 345/173 |
| 6,314,211 B1 | 11/2001 | Kim et al. | |
| 6,411,851 B1 * | 6/2002 | Winkler | 607/30 |
| 6,428,487 B1 * | 8/2002 | Burdorff et al. | 600/568 |
| 6,561,333 B2 * | 5/2003 | Larson et al. | 192/41 S |
| 6,791,601 B1 | 9/2004 | Chang et al. | |
| 6,824,539 B2 * | 11/2004 | Novak | 606/1 |
| 2001/0055197 A1 * | 12/2001 | Agata et al. | 361/683 |
| 2002/0026093 A1 | 2/2002 | Ooyatsu | |
| 2002/0062062 A1 | 5/2002 | Belson et al. | |
| 2002/0097210 A1 * | 7/2002 | Lonoce et al. | 345/87 |
| 2002/0149706 A1 * | 10/2002 | Rosen | 348/794 |
| 2002/0193676 A1 * | 12/2002 | Bodicker et al. | 600/407 |
| 2003/0025789 A1 * | 2/2003 | Saito et al. | 348/76 |
| 2003/0052787 A1 * | 3/2003 | Zerhusen et al. | 340/573.1 |
| 2003/0060678 A1 * | 3/2003 | Watai et al. | 600/109 |
| 2003/0067744 A1 * | 4/2003 | Pappalardo et al. | 361/686 |
| 2003/0076410 A1 * | 4/2003 | Beutter et al. | 348/65 |
| 2003/0103324 A1 * | 6/2003 | Gallivan | 361/681 |
| 2005/0147399 A1 | 7/2005 | Kimura et al. | |
| 2005/0283048 A1 * | 12/2005 | Gill et al. | 600/121 |

FOREIGN PATENT DOCUMENTS

| | | |
|---|---|---|
| JP | 3066423 A | 3/1991 |
| JP | 8508597 T | 9/1996 |
| JP | 10248805 A | 9/1998 |
| WO | 9423375 A1 | 10/1994 |
| WO | WO 00/44276 | 3/2000 |
| WO | 0074052 A1 | 12/2000 |
| WO | 2005085992 A1 | 9/2005 |

* cited by examiner

FIG. 8

CAPTURE₁

STORZ KARLSTORZ

INFORMATION
FRIDAY, NOVEMBER 30, 2001 08.00.01
PATIENT (FIRST)   (LAST)
BIRTHDATE   DATE OF TREATMENT
PATIENT ID
SURGEON
REMARKS

DISC STATUS
STILL   33
VIDEO   00:32:07
SPACE REMAINING   24.47MB

CONTROL PANEL

FIG. 10

CAPTURE₁

INFORMATION
FRIDAY, NOVEMBER 30, 2001 08.00.01

PATIENT (FIRST) (LAST)
JOHN    DOE

BIRTHDATE    DATE OF TREATMENT
07-12-1960   01-01-2001

PATIENT ID
01-4358973235

SURGEON

REMARKS
HEART RATE NORMAL

DISC STATUS
STILL  33
VIDEO  00:32:07
SPACE REMAINING  24.47MB

CONTROL PANEL

FIG. 11

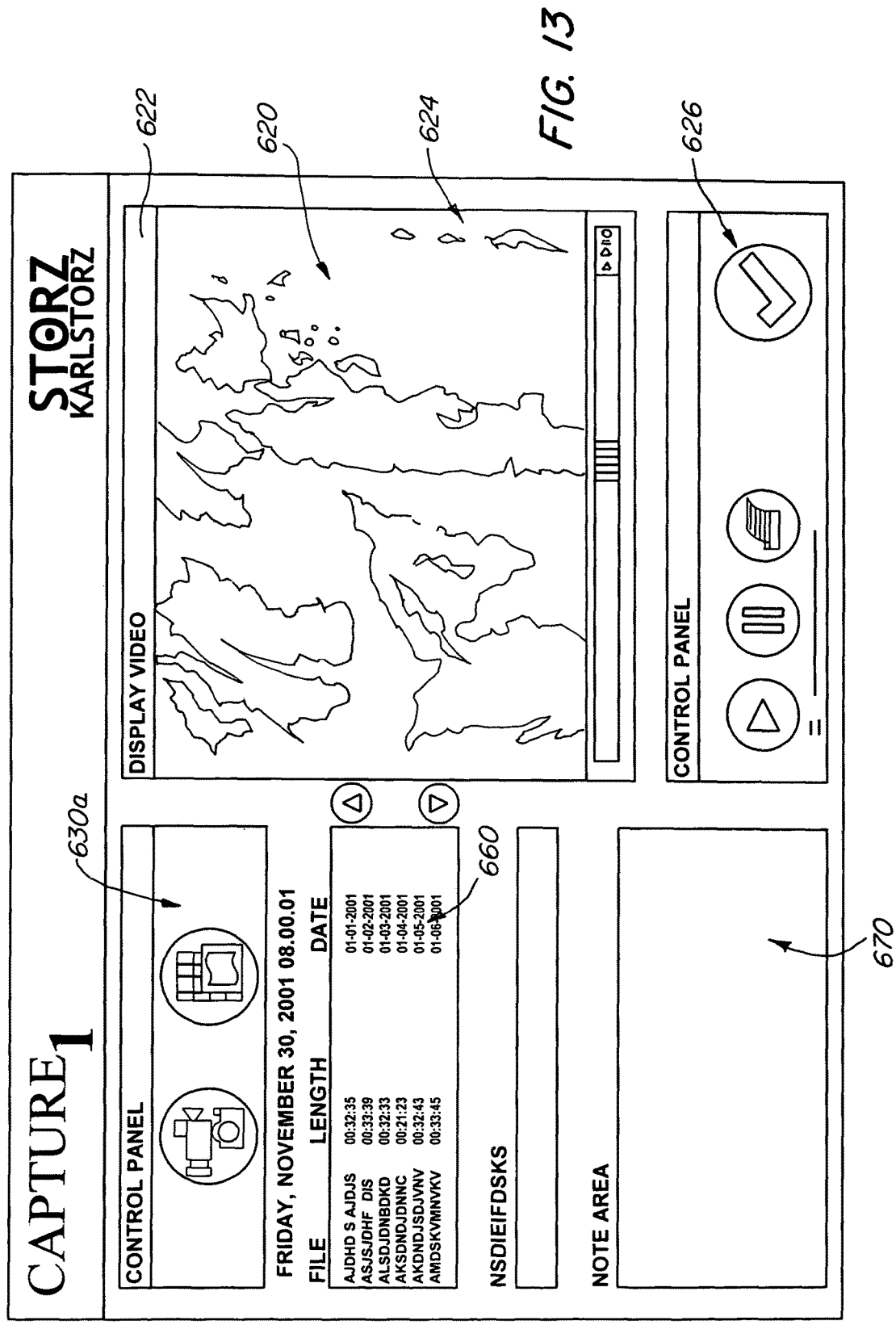

VIDEO RECORDING AND IMAGE CAPTURE DEVICE

PRIOR APPLICATION

Applicant claims priority benefits under 35 U.S.C. § 119(e) of U.S. Provisional Patent Application Ser. No. 60/410,456 filed Sep. 13, 2002.

FIELD OF THE INVENTION

The invention relates generally to device for video recording and image capture, and more particularly to such a device for image based documentation of surgical procedures. The invention also relates to means to process signals into an MPEG layer stream.

BACKGROUND OF THE INVENTION

The maxim that "a picture is worth a thousand words" is more true than ever in image based documentation of surgical procedures. There patients' lives and physicians' reputations are at stake. The early history of image based documentation is littered with crude attempts at utilizing photographic film to capture anatomical curiosities and groundbreaking surgical advances for teaching purposes. However, little attempt was made to provide documentation of routine cases. Average patients simply did not merit this special consideration.

With the advent of analog cameras coupled to fiber optics, physicians began displaying some surgical patient images on video monitors in the operating room. This was especially true in endoscopic surgeries where physicians peer inside patients' body cavities normally only viewable with open surgery. Attempts made to systematically record all patient procedures on videotape required large and cumbersome archives of videotapes.

Although analog cameras are still used, solid state image cameras coupled to endoscopes and other medical instruments are now standard. These cameras produce images in digital format. Such format allows convenient and efficient image transfer, review, and archival.

One method for archiving digital images is suggested in U.S. Pat. No. 6,067,075 to Pelanek. Therein, a workstation is disclosed for transferring and archiving patient images previously stored in the memory of diagnostic equipment. However, this method does not disclose contemporaneously saving images in a permanent location, meaning that the equipment is subject to "downtime" as data is extracted from its memory.

Once image data has been extracted and archived it must be made available to those in a position to best make use of it, the treating physician. Ironically in a circular manner, the person to whom eventual delivery of images is made is the same person who used the diagnostic equipment to record the images in the first place who must now await it being made available to him. Thus, it would be advantageous to the physician to have the data available at the conclusion of the surgical procedure or series of surgeries. Consequently, equipment downtime for data extraction also is eliminated increasing efficiency of equipment and facility utilization.

Image data availability, however, is only of value when the data can be read and images displayed readily. Thus, exotic and unusual methods of storing and reading image data chain physicians. Most convenient are displays in NTSC and PAL standards and devices that can play image data on these displays. NTSC is the common television standard in the U.S., while PAL standards predominate in Europe and in parts of Asia. Additionally, most convenient for medical personal, is for images and video to be viewable utilizing common off-the-shelf optical media players (i.e. set-top DVD players) and/or standard personal computers.

U.S. Pat. No. 5,045,955 to Ikeda discloses an apparatus coupled to a digital tape drive for recording and reproducing high-definition medical images having specific analog matrix exceeding that of NTSC or PAL standards. Typically, these images can only be produced by specialized imaging equipment and can only be viewed on highly specialized monitors. They are incompatible with NTSC or PAL standards and thus are inapplicable to the use of documenting procedures where analog or digital cameras provide a video signal to be displayed.

Other suggestions have been made to integrate images into a medical setting. Therein, imaging is primarily related to diagnosis rather than documentation; resulting in files solely consisting of visually relevant components and omitting narration by the treating physician.

Suggestions to incorporate equipment in surgical suites fail to consider issues relevant to logistics of placing equipment. Surgical suites include a plurality of equipment. Vertically stacking equipment in shelves, i.e. racking, advantageously conserves space. However, this limits the readily available user-operator access to front face plates. Equipment that incorporates space saving advantages while providing maximum user-operator access, therefore, is highly desired.

Therefore, what is desired is a device that produces and saves a surgical documentary recording file that incorporates both video and audio to a transportable and common media contemporaneously during the surgery.

What is also desired is a device that formats a video signal into a plurality of video formats for display, displays an image stream, and allows a user to capture still images and save same as a still graphic file to the same media as the documentary recording file.

It is further desired that the device and the parts that the user interacts with are convenient and accessible.

Also, it is desired that the device is capable of "feed through" of real-time video signals to a plurality of display devices, in a plurality of video formats, when the device is in a standby mode, when the device is off, or in the event when the device malfunctions.

Further, what is desired is an interactive tutorial which allows a user to manipulate the files saved.

These and other objectives are met by the embodiments of the present invention.

SUMMARY OF THE INVENTION

In accordance with one embodiment, a device for medical video recording includes an endoscope, and an imager for converting energy such as electromagnetic energy, direct current energy and the like, which is received from said endoscope to signals that are contemporaneously stored onto said media.

In accordance with one embodiment of the invention, a device is provided that encodes a video signal into a documentary recording file formatted in an MPEG-2 layer.

In accordance with one embodiment of the invention, a multimedia interface to process a video signal and audio signal into a first and second digital data stream having common characteristics is provided.

In accordance with one embodiment of the invention, a recording mode for recording a video stream during a surgical procedure is provide for surgical documentation.

In accordance with one embodiment of the invention, a means for a video signal to be displayed by a display unit during recording mode, or when the device is in a standby mode, or when the device is off, or when the device has malfunction, is provided.

In accordance with one embodiment of the invention, an archival mode is provided for review, edit and playback of a documentary recording file and graphic file.

In accordance with one embodiment of the invention, a medical instrument having touch screen control includes a touch screen for entering control commands, a processor for receiving the control commands and for generating control signals to operate the medical instrument, a housing for enclosing the processor. The touch screen is movable between a first position protected by the housing and second position extended from the housing for entry of the control commands.

In accordance with one embodiment of the invention, a multimedia interface for processing a video signal for recording video into a multiple frame layer includes a controller for an inter-ic bus for providing a multiple master digital connection, an analog to digital converter for converting a video signal to a first digital stream, the converter operably connected to the inter-ic bus, a video compression and decompression integrated circuit for encoding the first digital stream into a second digital stream having frames and decoding a second digital stream, the video compression and decompression integrated circuit operably connected to the inter-ic bus a programmable buffer for selectively saving frames handled by the controller, the buffer operably connected to the controller and the video compression and decompression integrated circuit and the buffer inserting the frame into the second digital stream for decoding.

In accordance with one embodiment of the invention, a method for recording an MPEG layer file for documenting surgical procedures while displaying an MPEG layer stream and n number selecting still image files corresponding to the MPEG layer stream, includes the steps of providing a first digital data stream comprising a video signal, providing a second digital data stream comprising an audio signal, multiplexing an MPEG layer data stream from the first and second digital data stream, streaming the MPEG layer data stream to a hard drive and an optical media drive operably connected on a vertically stacked bus, writing the MPEG layer stream to the hard drive and the optical media drive, displaying the MPEG layer stream on a display unit, selecting n number of frames from the MPEG layer stream, converting n frames to n still image files, and multiplexing the output signal to the display unit by adding n still image files.

The terms "communicate", "communicating" and "communication" as used herein include both conveying data from a source to a destination, as well as delivering data to a communications medium, system or link to be conveyed to a destination. The term "communication" as used herein means the act of communicating or the data communicated, as appropriate.

The invention and its particular features and advantages will become more apparent from the following detailed description considered with reference to the accompanying drawings.

BRIEF DESCRIPTION OF THE DRAWINGS

FIGS. 8 through 13 depict use of a Video Recording and Image Capture Device through the interactive display of the touchscreen of FIG. 1;

DETAILED DESCRIPTION OF THE DRAWINGS

The present invention will be described as used in connection with one or more endoscopes. It will be understood that other applications may be used equally effectively. Various frame displays and icons having particular graphical representations are described in connection with the functions of the present invention. It will be understood that other graphical representations may be used equally effectively in communicating to users the function performed therein.

Herein, image and image stream refer to the perception of the user utilizing their audiovisual capabilities; an image stream may also include an auditory component. Video signal, digital signal, analog signal, data stream, or the like refer to electrical signals in the present invention and electrical equipment operably connected and/or associated with the present invention.

Figure 1:
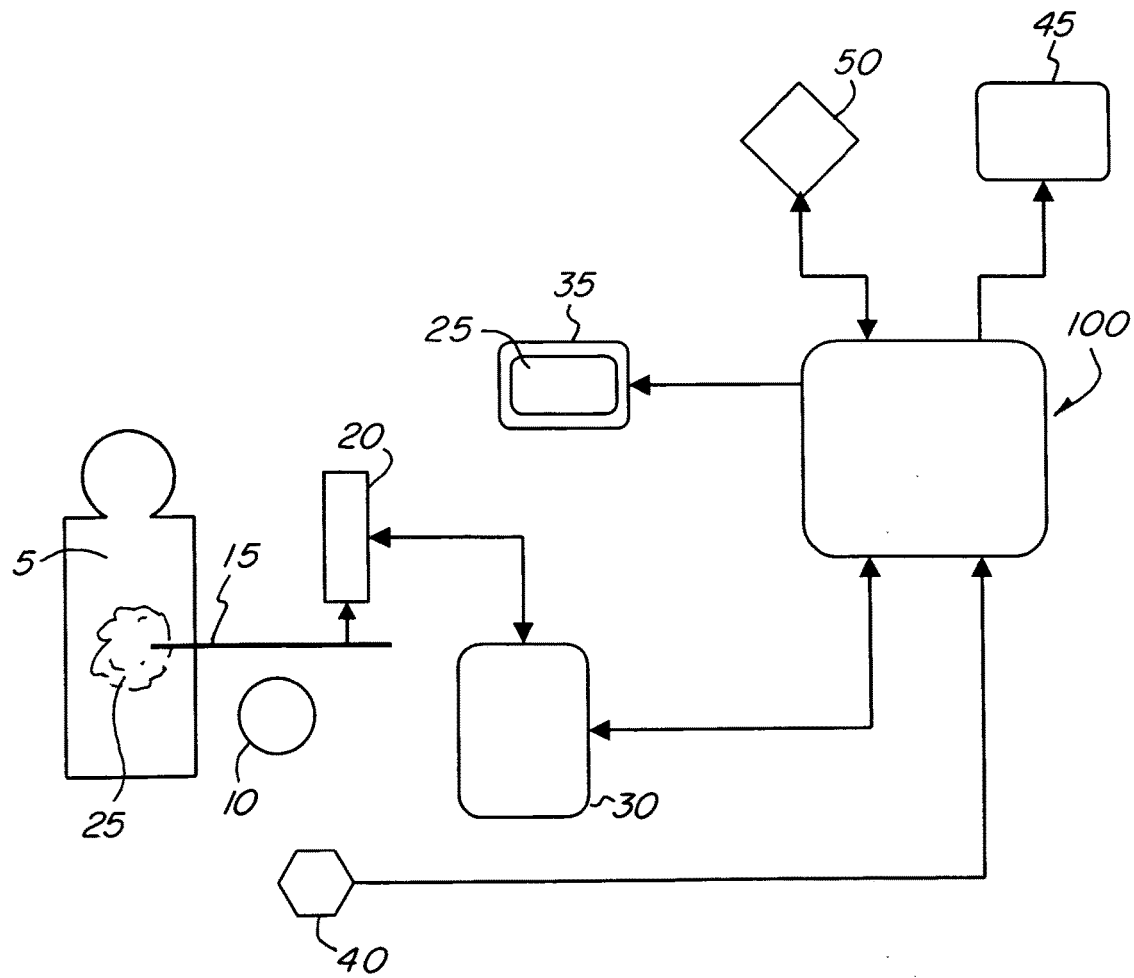
FIG. 1 is a schematic diagram of a Video Recording and Image Capture Device used in a surgical patient setting in accordance with the present invention.

FIG. 1 is a schematic diagram of a Video Recording and Image Capture Device used in a surgical patient setting in accordance with one embodiment of the present invention. Patient 5 is being examined by user 10 with an endoscope 15. User 10 may be a physician, surgeon, nurse, or other qualified professional or para-professional. Video Recording and Image Capture Device (imager) 100 has been placed into a video recording mode. A camera head 20, such as a charge coupled device (CCD), CMOS, or CCI chip, is coupled to endoscope 15 to receive and produce a video signal 300 (see FIG. 4) of a body cavity of patient 5. Video signal 300 results in an image stream 25 when displayed on a display unit.

As user 10 manipulates endoscope 15, user 10 controls camera head 20 with camera control unit (CCU) 30 and observes image stream 25 on a display unit, for example external video screen 35. Imager 100 is operably connected to CCU 30 to receive video signal 300. Device is also operably connected to external video screen 35, microphone 40, printer 45, and network 50 through standard ports. In one embodiment, imager 100 is operably connected to camera head 20 to receive video signal 300 and control camera head 20, obviating the need for CCU 30.

As user 10 examines and treats patient 5, imager 100 is recording a digital data stream representing image stream 25 on optical media drive (OMD) 125 (see FIG. 2) and saving a backup copy to hard drive (HDD) 120 (see FIG. 4) for a plurality of purposes. During this period user 10 may provide narration to the examination. Microphone 40 or an independent audio recording system captures the narration and converts it into audio signal 314$i$ (see FIG. 6) or 316$i$ (see FIG. 6), respectively, collectively audio signal 315 (see FIG. 6).

Upon encountering a situation requiring further investigation, user 10 utilizes an image capture mode to save and freeze a first image from image stream 25 for further investigation. Using imager 100, a second image substantially like the first image can be superimposed on image stream 25. Upon encountering further situations that attracts the attention of user 10, a plurality of second images substantially corresponding to respective first images found of interest can be saved and concurrently superimposed on image stream 25. A file corresponding to second image can be printed with printer 45 and/or forwarded over network 50 to other persons for consultation.

Figure 2:
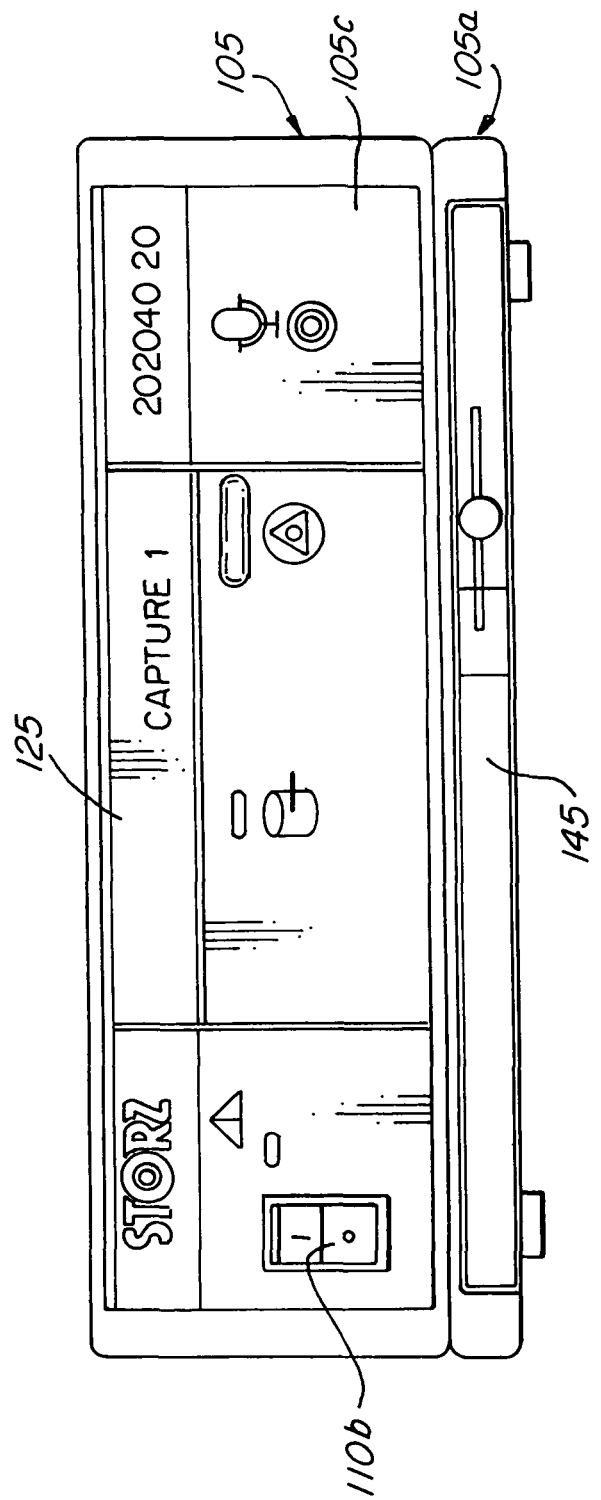
FIG. 2 depicts a front panel elevation view of a Video Recording and Image Capture Device of FIG. 1.
Figure 3:
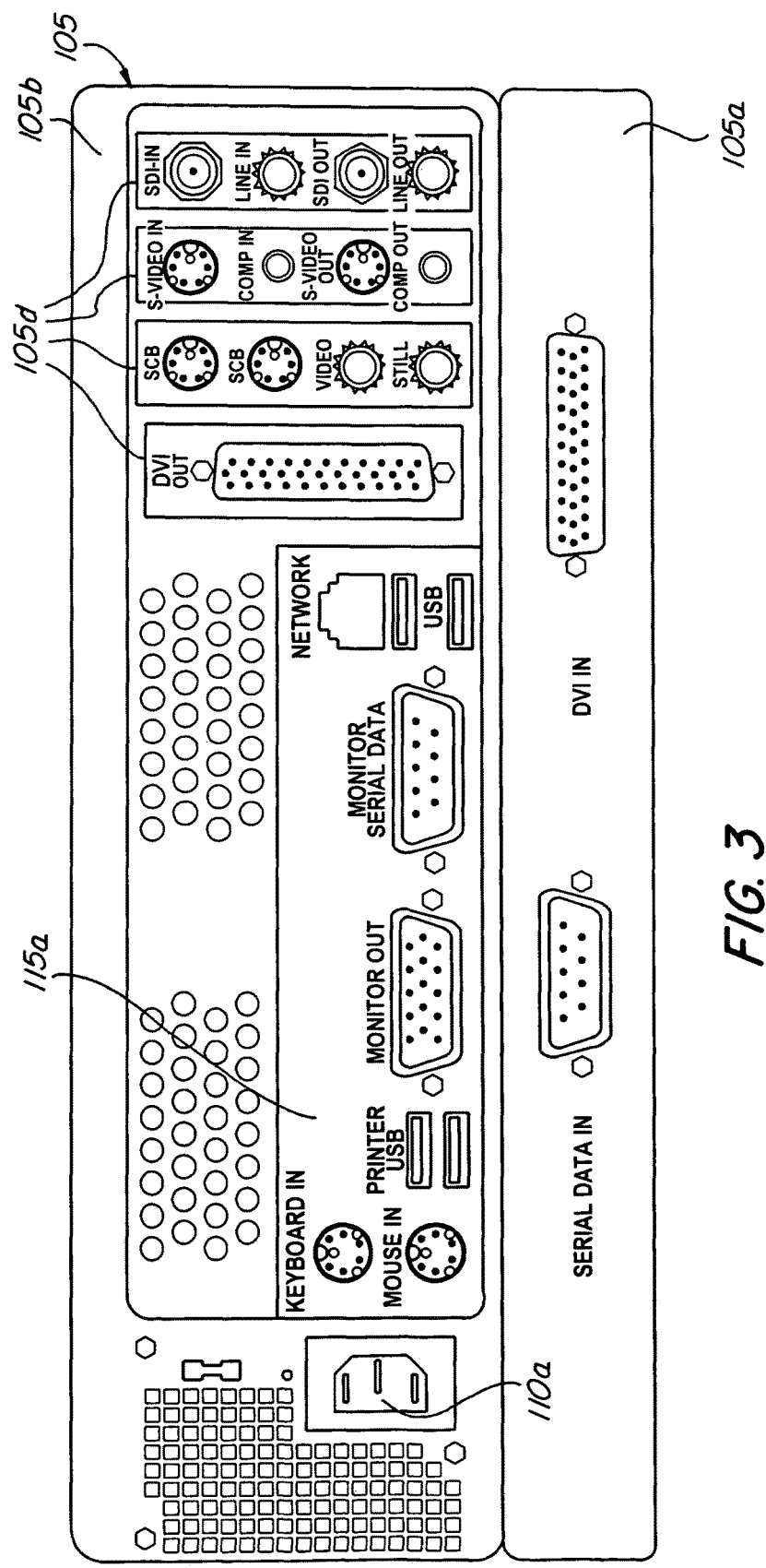
FIG. 3 depicts a rear panel elevation view of a Video Recording and Image Capture Device of FIG. 1.
Figure 4:
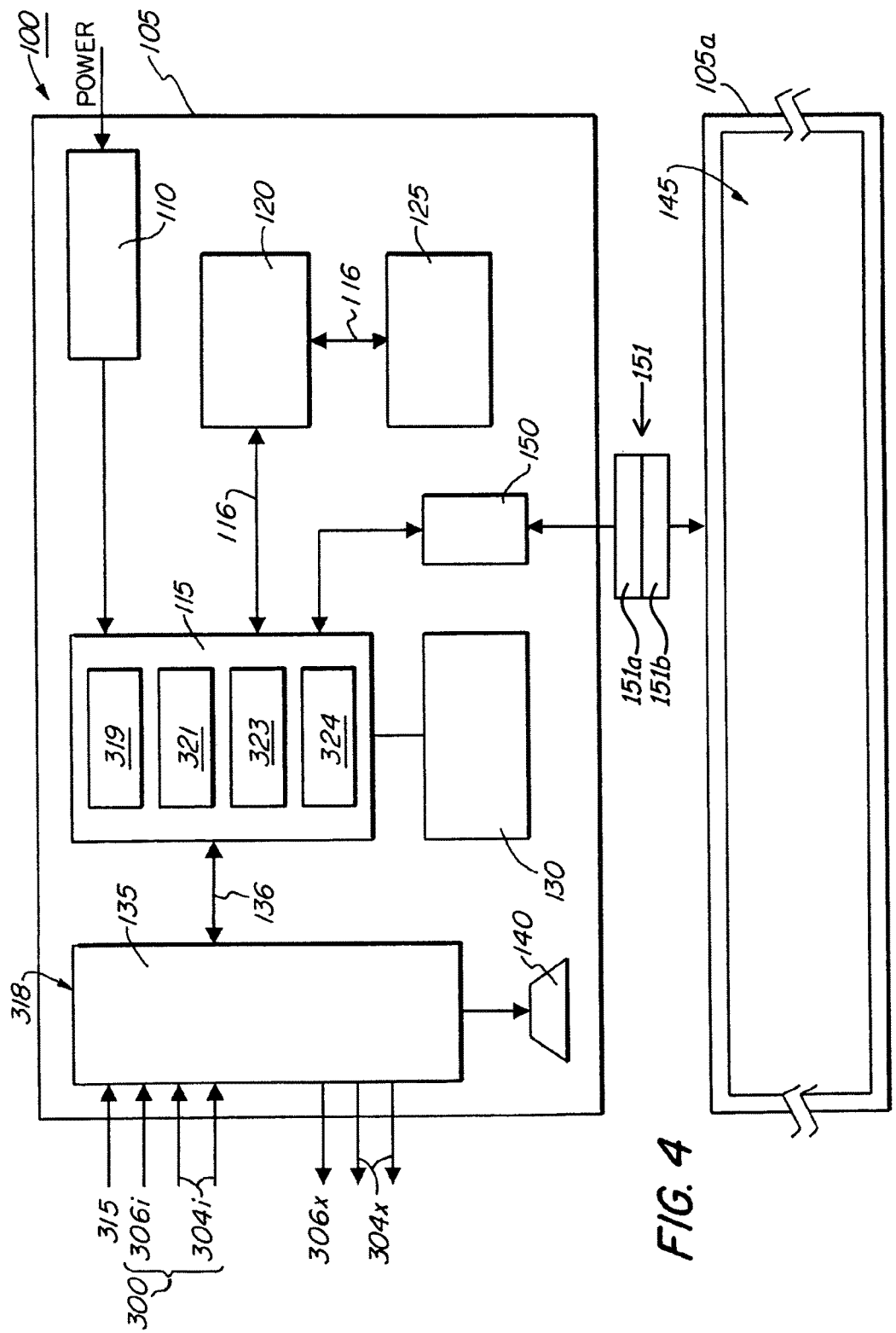
FIG. 4 is a schematic diagram of a Video Recording and Image Capture Device of FIG. 1.

FIGS. 2 and 3 depict a front panel and rear panel elevation view, respectively, of a Video Recording and Image Capture Device in accordance with one embodiment of the present invention. FIG. 4 is a schematic diagram of a Video Recording and Image Capture Device in accordance with one embodiment of the present invention. Imager 100 is substantially housed in chassis 105 and includes a plurality of components: power supply 110, microprocessor main board (MMB) 115, hard drive (HDD) 120, optical media drive (OMD) 125, communication interface 130, multimedia interface 135, speaker 140, digital video interface 150. Chassis 105 includes an add-on tray 105$a$ that advantageously houses touchscreen 145.

Power supply 110 is connected to an AC power supply with an electric cord at power port 110$a$ located on chassis back panel 105$b$. When power switch 110$b$ of chassis front panel 105$c$ is engaged, power supply 110 provides suitable power to components of imager 100. Power supply 110 conforms to IEC 601-1 isolation requirements, provides power meeting medical grade standards of 145 Watts, includes a power correction factor, and is capable of automatically handling automatically an AC voltage range of 100 to 250 VAC, 50-60 Hz.

Microprocessor main board (MMB) 115 executes software and includes a central processor unit ("processor"), random access memory, a plurality of expansion slots, a BIOS chip, and on-board sound and graphics capabilities on a footprint convenient for chassis 105. Therein, it may be that an Intel Pentium III with a processing speed of at least 800 MHz; an Intel 815 chip set; at least three (3) PCI and one (1) AGP slot; SDRAM of at least 128 MB; on-board AGP graphics; and a flash upgradeable BIOS chip wherein a customized logo may be loaded, is provided on an ATX motherboard. Further, MMB 115 preferably includes port panel 115$a$ to connect to other devices and or networks via serial, parallel, USB and ethernet, and to connect to mouse, keyboard, and video monitor; a Intel 40-pin DVO motherboard connector, or similar, and support for the connector.

Hard drive (HDD) 120 and optical media drive (OMD) 125 maybe IDE or Enhanced IDE (alternatively IDE) compatible data storage media drives operably connected MMB 115 by a vertically stacked IDE bus 116. HDD 120 maybe a magnetic hard drive having at least 40 Gigabytes of storage and minimal access time, as such a drive from Maxtor having EIDE access time of 8.0 ms, 7200 rpm disk speed is preferred. OMD 125 is preferably a DVD+RW drive capable of reading and writing data to an optical media disk, such as a compact disk (CD) and/or a digital versatile disk (DVD).

Communication interface 130 is any kind of network or proprietary communications interface. Therein, for example, a network card that is capable of interfacing with the Karl Storz®, Inc. Storz Communication Bus (SCB) is preferred.

Multimedia interface 135 connects to MMB 115 via a Peripheral Component Interconnect (PCI) local bus to provide record and write image stream 25 originating from camera head 20. Speaker 140 is housed in chassis 105 and provides auditory capabilities for imager 100.

Digital video interface 150 is operably connected to MMB 115 to create a video signal conforming to the digital visual interface (DVI) standard. Therein, a digital video interface 150 is preferably physically implemented as a printed circuit board having an Intel 40-pin DVO connector, or similar, to MMB 115 and a DVI-D output connector in expansion slot 105$d$. As illustrated in FIG. 4, touch screen 145 may advantageously be coupled to digital video interface 150 by means of plug 151. In this manner, touch screen 145 is unpluggable from the housing. Additionally, it is contemplated that plug 151 may comprise stackable mating plug portions 151$a$, 151$b$.

Figure 5A:
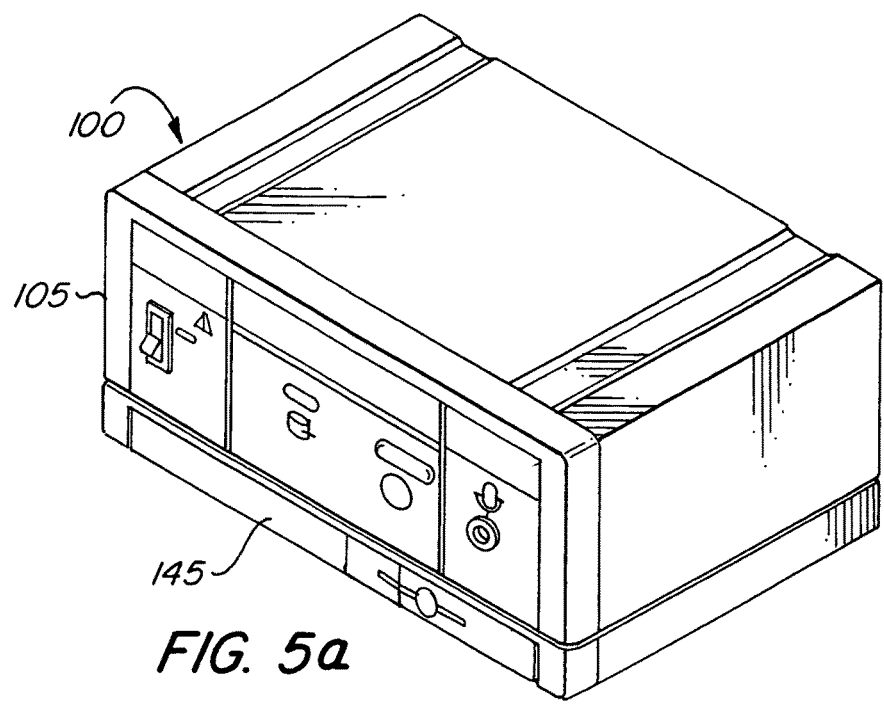
FIGS. 5a, 5b, and 5c depict a Video Recording and Image Capture Device of FIG. 1.
Figure 5B:
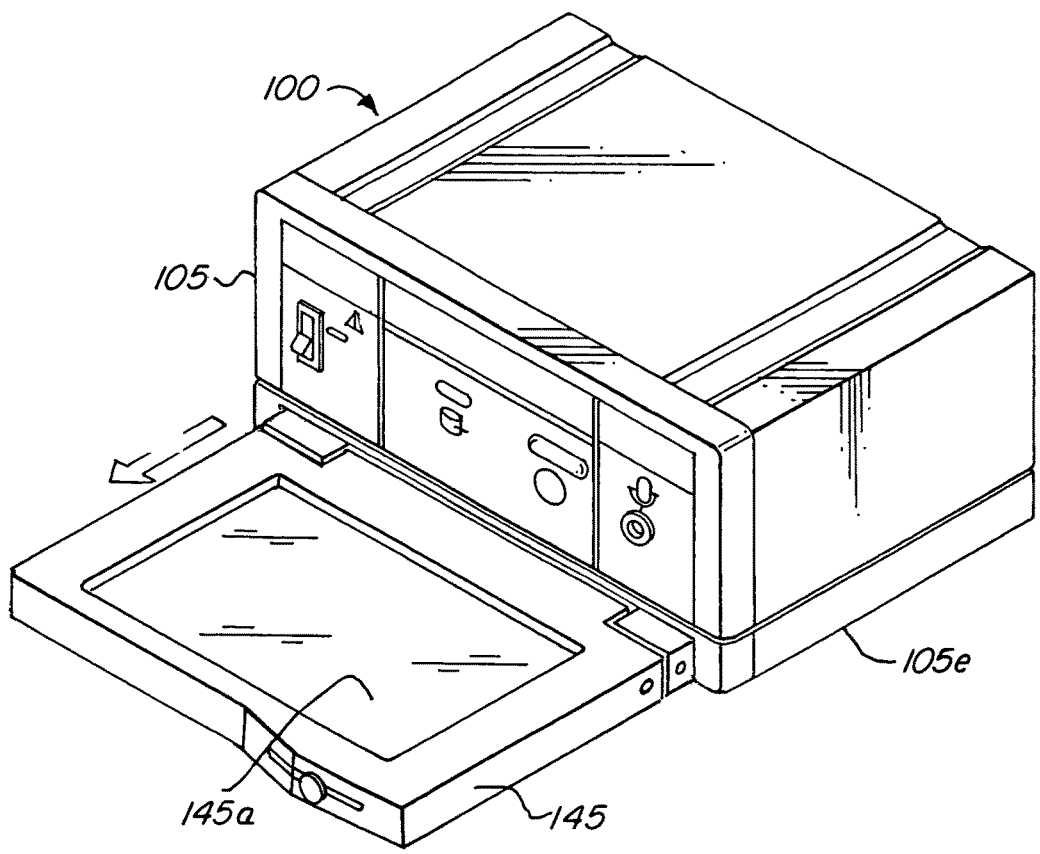
Figure 5C:
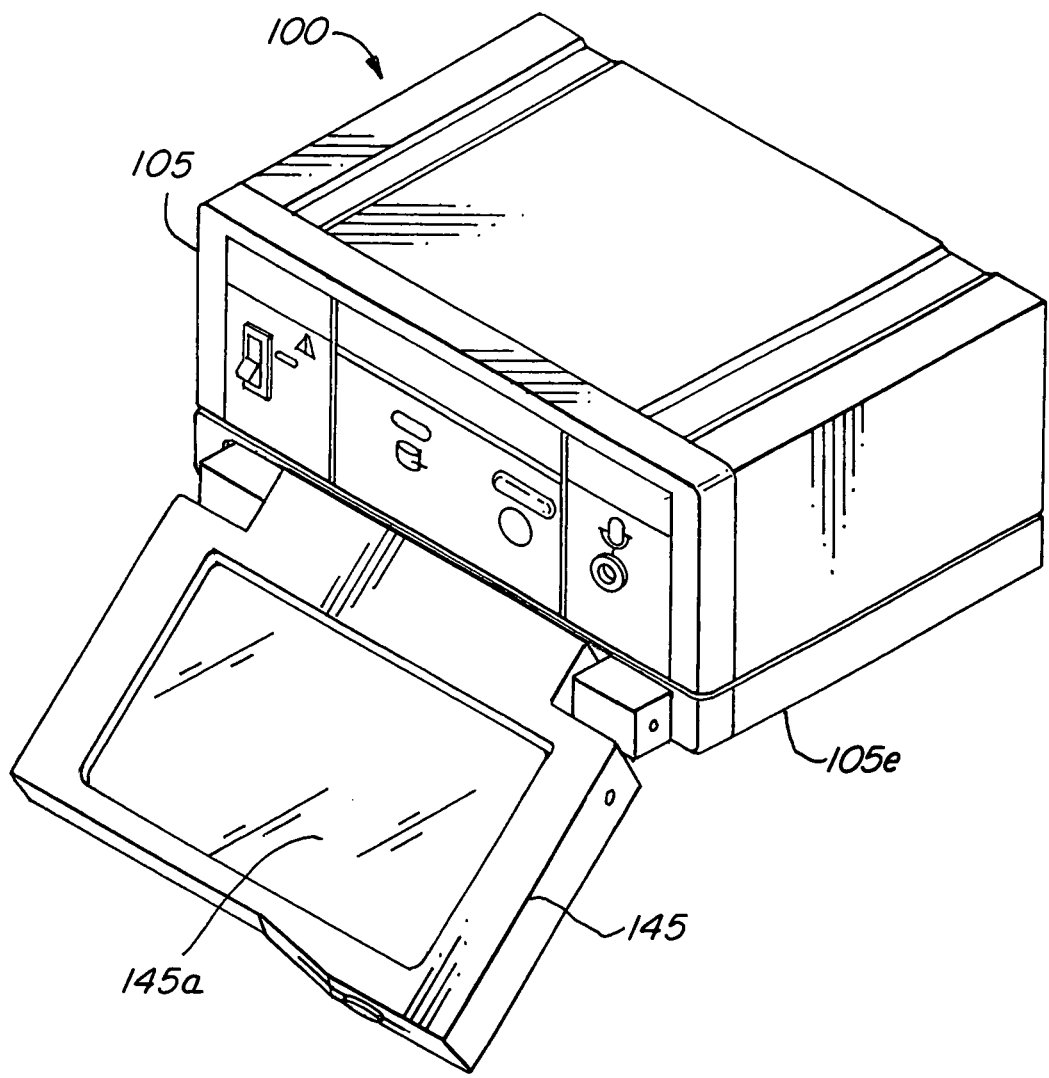

A touchscreen 145 is provided as illustrated on FIGS. 5$a$, 5$b$, and 5$c$ in accordance with one embodiment of the present invention. A surface 145$a$ responsive to touch by an operator, such as user 10, and a display 400 capable of showing the functions of imager 100 are included in touchscreen 145. Preferred is a touchscreen manufactured by Optrex Inc. of Plymouth, Mich. A video connection to MMB 115 is made to the corresponding DVI-D output and a data and power connection is made between standard RS-232 serial ports.

Touchscreen 145 is advantageously housed in tray 105$a$ (see FIG. 14$a$) of imager 100 within chassis 105. Therein, it is mounted within a track advance system (TAS) 146 (see FIG. 14$a$) so that touchscreen 145 is secure and is relatively flush with a front face of chassis 105 as depicted in accordance with one embodiment of the present invention in FIG. 18.

TAS 146 allows user 10 to advantageously use the space available when equipment is racked. User 10 presses a button or other releasing mechanism to release touchscreen 145 and slides touchscreen 145 away from chassis 105 and out of tray 105$a$ as indicated by the arrows as depicted in accordance with one embodiment of the present invention in FIG. 5$b$. To make touchscreen 145 more user friendly and visible, user 10 is able to tilt touchscreen 145 at an angle as indicated by the arcuate arrows in accordance with one embodiment of the present invention in FIG. 5$c$.

Figure 15:
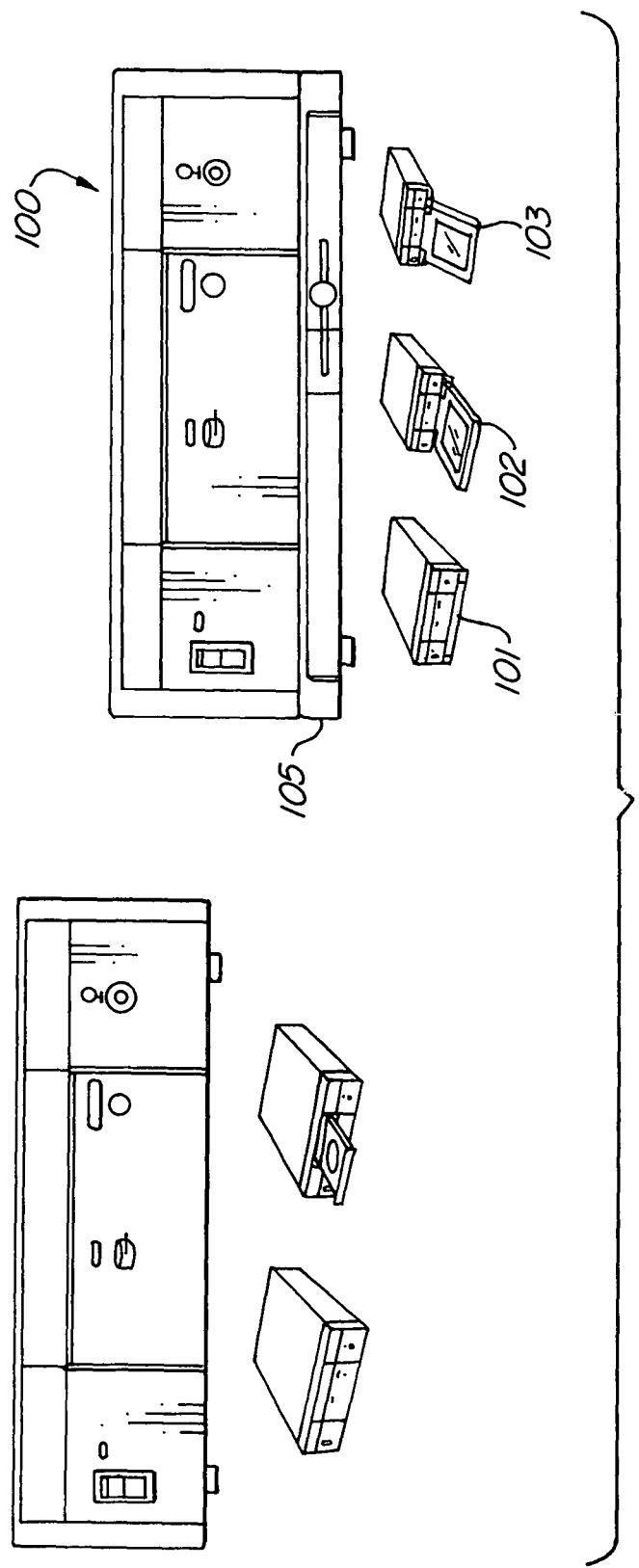
FIG. 15 depict a Video Recording and Image Capture Device of FIG. 1 with touch screen fully retracted, touch screen extended and touch screen extended and deflected.

FIG. 15 discloses the touch screen in various states of deployment. For example, 101 shows one embodiment in which the touch screen is fully retracted, however, other embodiments will not have the touch screen fully retract. 102 shows the touch screen extended out and 103 shows the touch screen extended out and deflected from the plane of the housing.

Figure 14A:
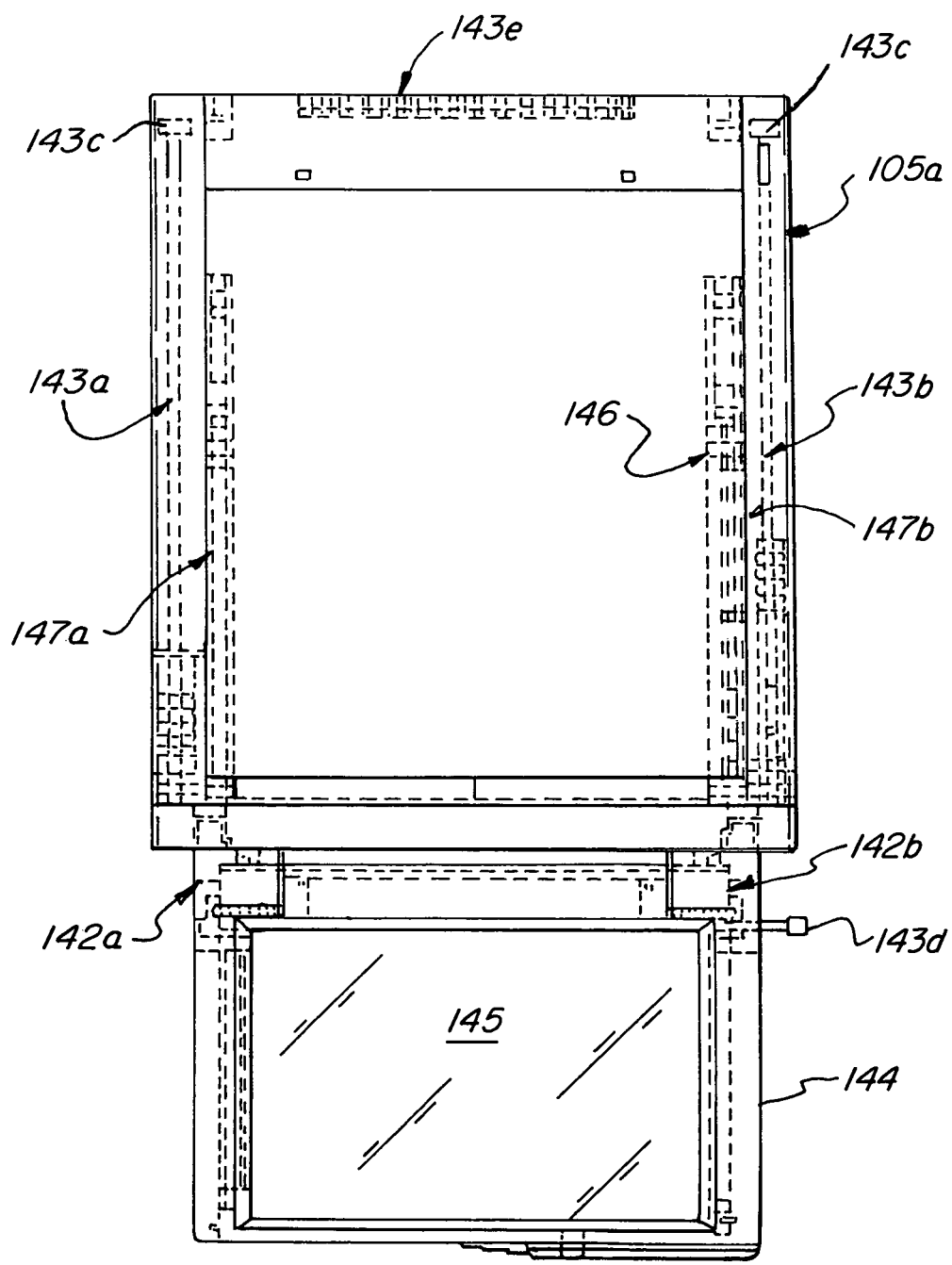
FIGS. 14a and 14b depict a plan view a track advance system for a touchscreen of a Video Recording and Image Capture Device of FIG. 1.

FIGS. 14$a$ and 14$b$ depict a plan view of a track advance system for a touchscreen of a Video Recording and Image Capture Device in accordance with one embodiment of the present invention. A platform 144 (shown advanced out of tray 105$a$) disposed to tray 105$a$ is operable with rails 143$a$ and 143$b$ and is guided by tracks 147$a$ and 147$b$ by bearings or other friction reducing mechanisms as depicted in accordance with one embodiment of the present invention in FIG. 14$a$. Releasing mechanism 143$d$ includes one or more components that selective to user desire, release touchscreen 145 in order to advance it. Releasing mechanism 143$d$ further may include one or more springs 143$e$.

Platform 144 may be of any suitable design to hold touchscreen 145 even when placed at an angle from horizontal. Touchscreen 145 is operative with imager 100 through cables and connectors.

Rails 143*a* and 143*b* have stops 143*c* (only partially shown for clarity) operable with tracks 147*a* and 147*b* to prevent advancing touchscreen 145 beyond a predetermined point.

Figure 14B:
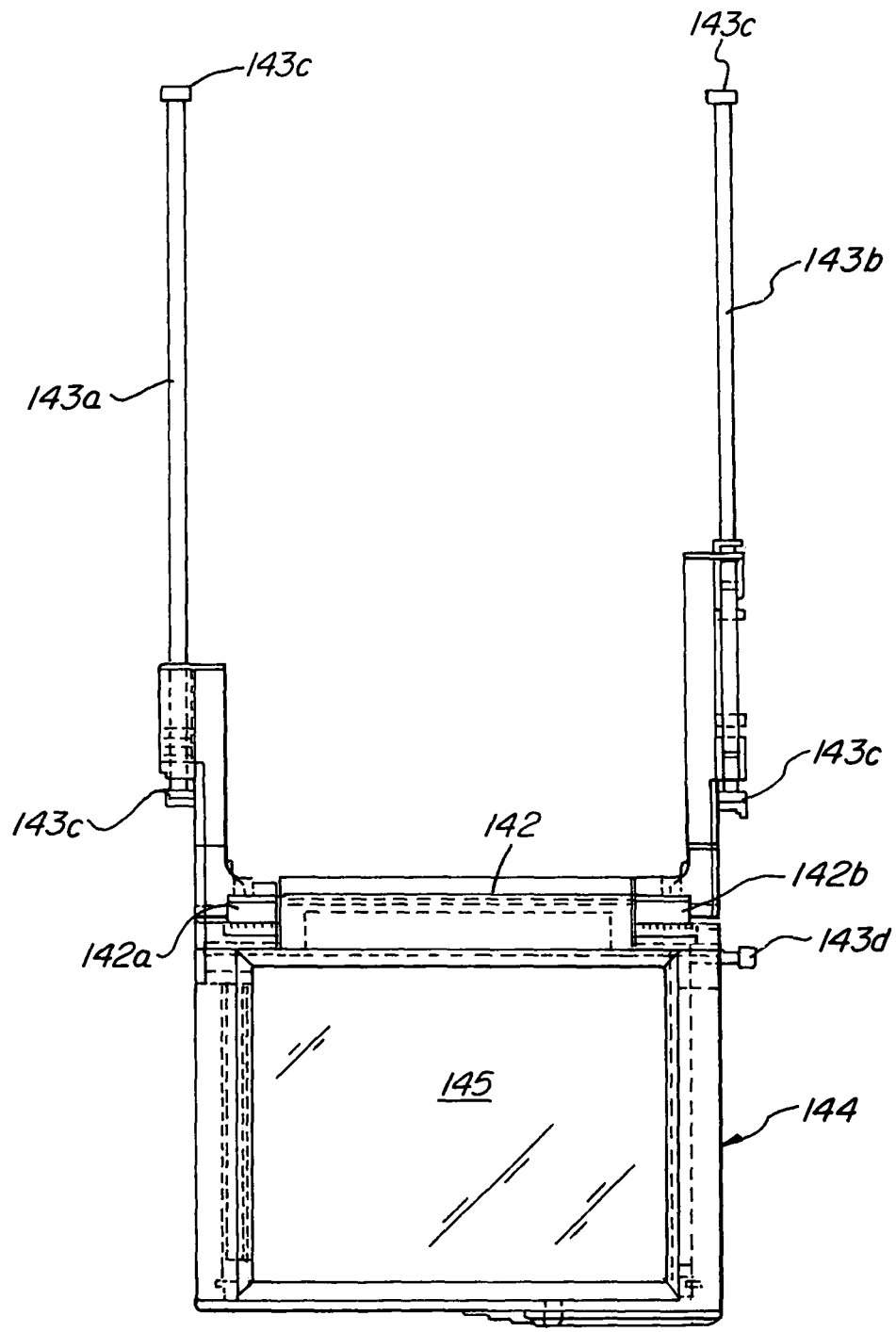

TAS 146 includes on or more hinge 142, such as edged hinge 142*a* and 142*b*, or center hinge 143*c* a center hinge as depicted in accordance with one embodiment of the present invention in FIG. 14*b*. Hinge 142*a* and 142*b* cooperate to angle platform 144 so that user 10 can during the surgery interactively access touchscreen 145. To prevent changing angle of the platform 144 or accidental closure, one or more tapping mechanisms are disposed with hinge 142, that make it resistant to unintentional movement.

Figure 6:
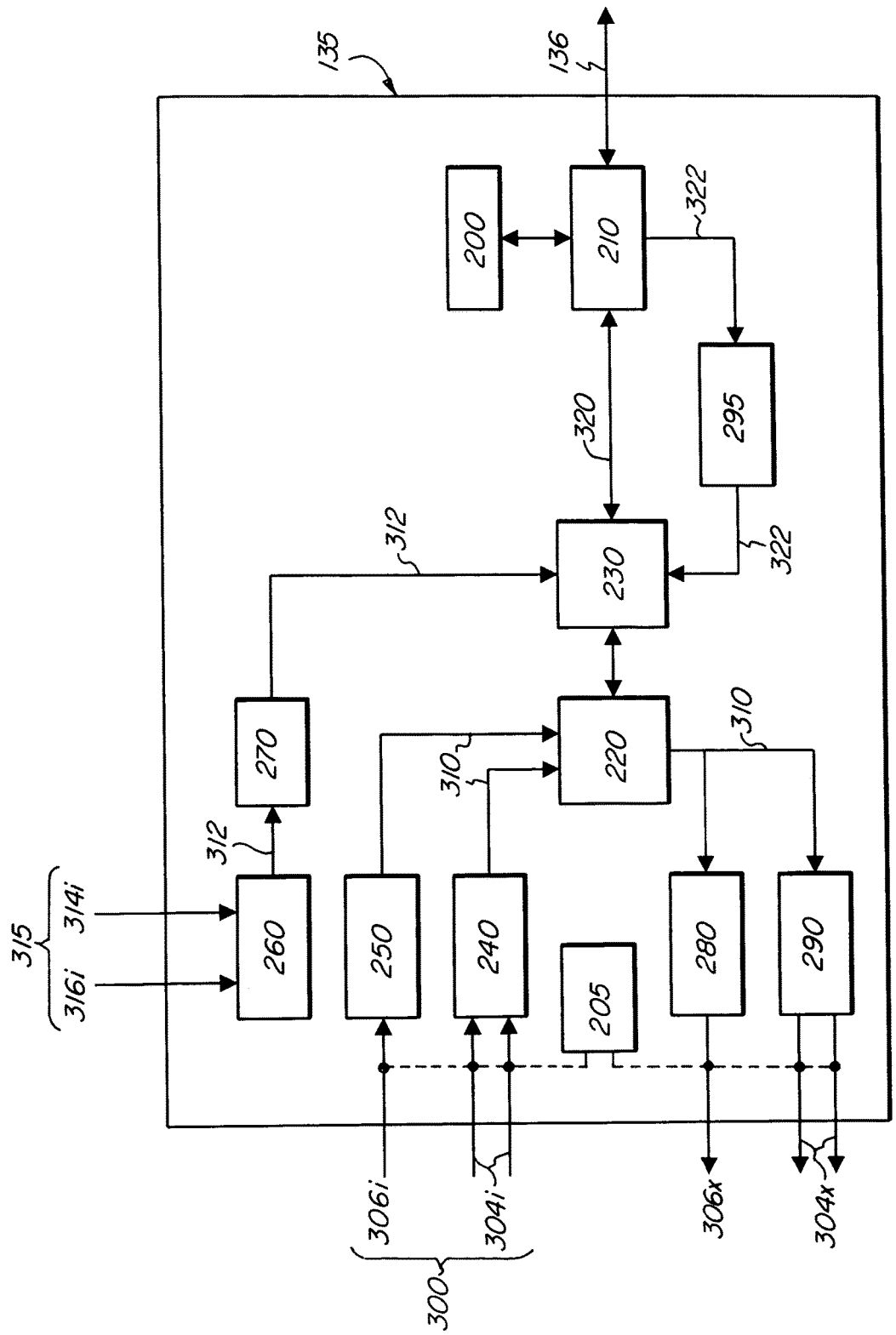
FIG. 6 is a schematic diagram of a multimedia interface of FIG. 1.

FIG. 6 is a schematic diagram of multimedia interface 135 in accordance with one embodiment of the present invention. Multimedia interface 135 is physically implemented on one or more printed circuit boards, also commonly referred to as expansion cards, having a plurality of integrated circuits and a PCI bus connection 136 to MBB 115 for data transfer. Through bus 136 multimedia interface 135 also receives electric power. Audio and video connection ports, i.e. input and output ports, are physically implemented in expansion slots 105 and integrally connected to multimedia interface 135. In one embodiment, multimedia interface 135 is implemented as a PCI expansion card with bus connection 136 to MBB 115 and a further printed circuit board connecting directly to the PCI expansion card.

Resident on multimedia interface 135 is an Inter-IC bus operatively controlled by controller 200. Controller 200 implements the Inter-IC bus as a multi-master bus to connect circuits to PCI interface 210. Router 220 is provided as a field programmable gate array and has programmable read only memory that is accessible via a port, such as a JTAG port.

In recording mode, imager 100 receives the input of video signal 300 and audio signal 315 and contemporaneously encodes both signals while writing the data stream to HDD 120 (see FIG. 4) and/or media in OMD 125 (see FIG. 4).

Video signal 300 is received by multimedia interface 135 as analog video signal 304*i* or digital video signal 306*i* in input ports located in expansion slot 105*d* (see FIG. 3). The active input port is automatically detected by multimedia interface 135, as are active output ports.

A relay 205 is operative to bypass video signal 300 to an exit port corresponding to the input port for display by an external monitor when imager 100 is not powered or imager 100 is in standby mode. Therein, relay 205 includes a receiver for receiving a sense signal from software to indicate that the recording mode is engaged. If the sense signal is not received with a predetermined time, video signal 300 is bypassed. If imager 100 is not powered, a default mode of relay 205 bypasses the signal to the corresponding port, i.e. video signal 300 input on the S-video input is bypassed to an S-video output port.

Analog video signal 304*i* is received using composite video input or S-Video input. If analog video signal 304*i* is received when imager 100 is not electrically powered or recording mode is not engaged, video signal 300 is bypassed using bypass relay 205. Received analog video signal 304*i* is digitized using analog to digital converter 240. Therein, the NTSC or PAL standard analog video signal 304*i* is digitized to first internal data stream, digital data stream (DDS) 310. A digitized data stream having 4:2:2 luminance to chrominance (YUV) pixels is preferred. Other data stream configurations may also be used. In particular, a data stream having 8:2:2 YUV may be advantageously used in connection with CCU 30 (see FIG. 1) which is capable of producing higher analog video frame quality. DDS 310 is then streamed via router 220 to video media compression and decompression integrated circuit (V-codec) 230 where it is encoded.

Digital video signal 306*i* is received using the SDI digital video signal input. If digital video signal 306*i* is received when imager 100 is not electrically powered or recording mode is not engaged, video signal 300 is bypassed using bypass relay 205. Received signal 306*i* is processed by SDI receiver 250 and converted to a first internal data stream, DDS 310. A digitized data stream having a 4:2:2 luminance to chrominance (YUV) pixels is preferred; although other data stream configurations may also be used. DDS 310 is streamed via router 220 to V-codec 230 where it is encoded.

Inputs for audio signal 314*i* originating from a stereo line and audio signal 316*i* originating from microphone 40 are provided for recording a desired audio signal such as dictation. Both inputs may be combined to create a single audio signal 315 or used individually. Audio signal 315 is received by audio compression and decompression integrated circuit (A-codec) 260 and converted to a second internal data stream, digital data stream for audio (DDSA) 312, and passed to automatic gain control 270 disposed on the Inter-IC bus. DDSA 312 is then streamed to V-codec 230.

V-codec 230 is provided as embedded software, preferably operating on a LINUX or UNIX embedded platform, on one or more integrated circuits on the Inter-IC bus and operatively connected to controller 200. Also operatively connected are one or more buffer memories, such as SDRAM integrated circuits. Configuration settings of V-codec 230 are stored on an associated erasable electronic programmable read only memory (EEPROM or EPROM) circuit, or similar. The embedded software of V-codec 230 executes an algorithm to decode and/or encode a Motion Picture Experts Group (MPEG) layer, such as MPEG, MPEG-2 and/or MPEG-4, data stream (MDS) 320. MDS 320 advantageously utilizes high compression rates achieved by using an index frame and noting a sequence of changes to that index frame in subsequent images. Therein, MDS 320 is comprised of a stream of frames 322.

Algorithms of this type are known to execute file formatting appropriate for CD-R and a plurality of DVD media storage and play. Typically, MDS 320 is preferred to encode in a file format designated as "VOB" applicable to DVD+RW media storage and play. It should be appreciated that the present invention may be adapted readily to utilize other compression and decompression algorithms.

V-codec 230 multiplexes DDS 310 and DDSA 312 into MDS 320 which is then streamed to MMB 115. From there, MDS 320 is streamed to HDD 120 and to OMD 125 via vertically stacked IDE bus 116. Therein, HDD 120 writes MDS 320 to a magnetic disk and streams a copy to OMD 125 for writing to an optical disk such as a CD-R or DVD media to create contemporaneous documentary recording file while the surgery is being conducted by user 10. If the write process on OMD 125 is interrupted or fails, a backup copy resides on HDD 120 for a subsequent write attempt after the conclusion of the surgery.

Figure 7:
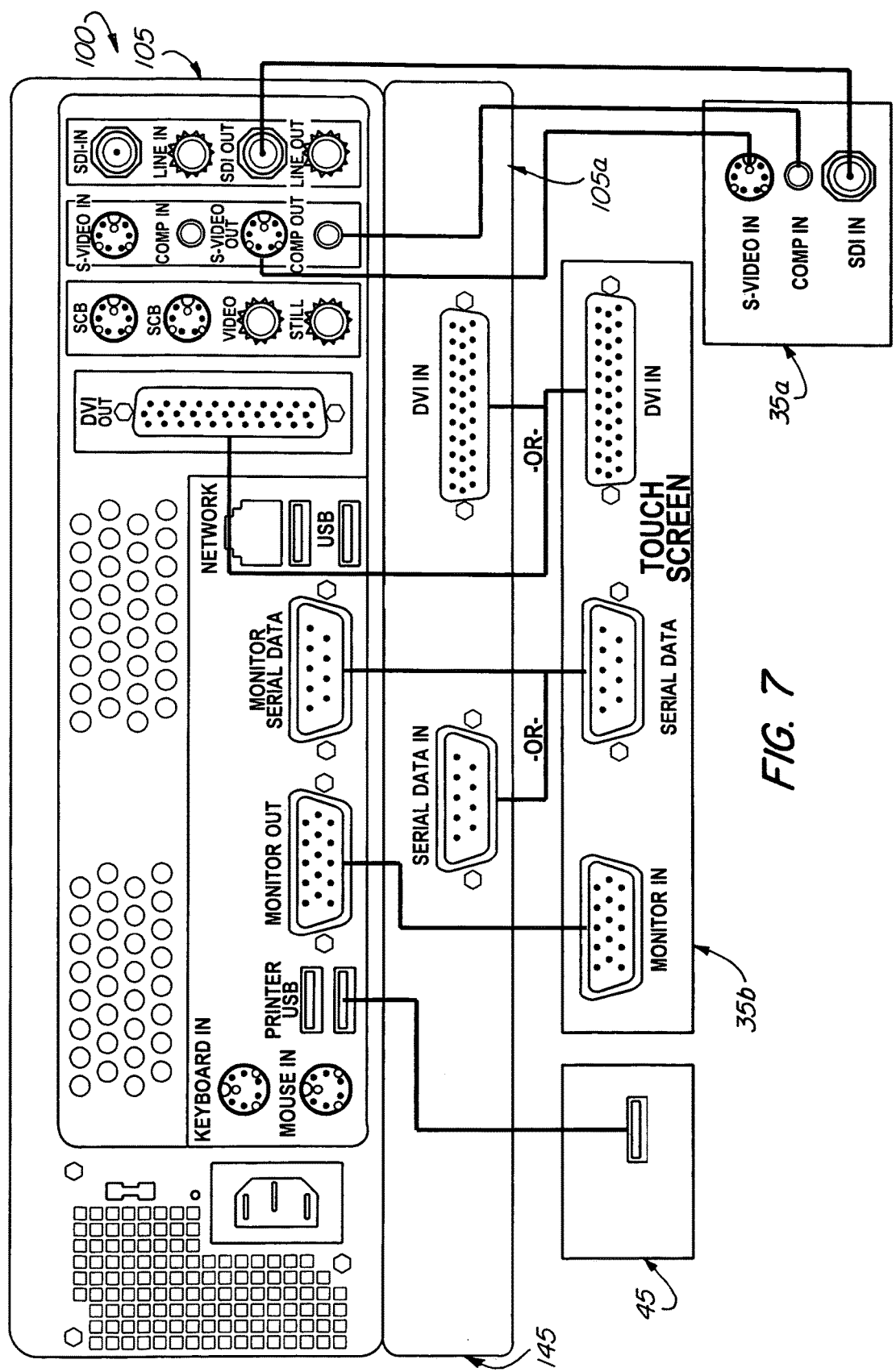
FIG. 7 depicts a schematic of interconnecting Video Recording and Image Capture Device and a display unit of FIG. 1.

A means for a video signal to be displayed by a display unit during recording mode is provided. The display unit may be external video screen 35 or touchscreen 145. FIG. 7 depicts a schematic of interconnecting imager 100 and a display unit in accordance with one or more embodiments of the present invention. An embodiment of video screen 35, external video screen 35*a*, is operable to receive an analog and/or digital signal using connectors for S-video, composite and/or SDI format. Therein, multimedia interface 135 senses the active output port and router 220 streams DDS 310 accordingly to either SDI transmitter 280 to produce digital video signal 306*x* or to digital to analog converter 290 to produce analog video signal 304*x*, respectively. In converter 290, common data stream DDS 310 is automatically converted to the appropriate NTSC or PAL standard analog signal in use by video screen 35*a*.

Touchscreen 145 is operable to receive a video signal in digital visual interface (DVI) format, and an embodiment of video screen 35, external video screen 35*b* having touchscreen capabilities, is operable to receive a video signal in digital visual interface (DVI) format or analog monitor format. Therein, MMB 115 streams a copy of MDS 320 to resident AGP graphics support and/or DVI graphics support and digital video interface 150 for output to touchscreen 145 and video screen 35*b* as required by the active output.

Image capture mode is provided for saving a frame 322 (see FIG. 6) from MDS 320 substantially like image of image stream 25. User 10 views an image of interest in image stream 25 and initiates instruction to "freeze" the image of interest. Since both reaction time on behalf user 10 and processing time on behalf of imager 100 has passed when such an instruction has been received, a frame 322 substantially like image 26 is saved, wherein the substantiality is temporal. The freeze instruction is forwarded to multimedia interface 135. Therein, controller 200 instructs PCI interface 210 to forward the current frame 322 being handled to frame buffer 295, also known as frame grabber, which stores frame 322.

Frame buffer 295 can be implemented as an integrated circuit, capable of storing and identifying a plurality n of frames 322 corresponding to maximum number n frames capable of being stored according to the buffer size (hereinafter frame 322$_1$ designating the first frame 322 stored, frame 322$_2$ the second . . . , and frame 322$_n$ the last frame stored). As shown, identification may be implemented by designating a first-in-first-out order, or similar order. Upon receipt of frame 322$_1$, buffer 295 forwards a copy to router 220. Router 220 multiplexes frame 322$_1$ with DDS 310 and streams the combined signal to the active output port for display as combined image. As described further herein in connection with image capture mode, user 10 is able to manipulate the position and size of the combined image within image stream 25 and on a display unit.

A copy of frame 322$_1$ is saved to HDD 120, preferably in file format Joint Picture Experts Group JPEG layer corresponding to the MPEG layer such as MPEG, MPEG-2 and/or MPEG-4 layer, as a graphic file. A software application for conversion to other formats such as "TIFF," "BMP," and/or "FPX", or similar, is provided.

Upon additional instruction by user 10 to capture further images, further corresponding frames 322 are saved in the manner described. Therein, frame 322$_2$ is multiplexed with frame 322$_1$ and DDS 310 and the combined signal streamed to the active output for display on a display unit.

An archival mode is provided for review, edit and playback of documentary recording file and a graphic file. Therein, the recording file is accessed and a digital data stream corresponding to MDS 320 is read from media of HDD 120 and/or OMD 125 and is streamed to V-codec 230 and is decompressed into a digital data stream corresponding to DDS 310. The decompressed digital data stream is then routed to the active port for display or transferred to MMB 115 for display on a display unit.

FIGS. 8 through 13 depict use of imager 100 through interactive display 400 of touchscreen 145 in accordance with one embodiment of the present invention. It should be appreciated that similar usage is achieved through use of other input devices, as for example mouse and keyboard, coupled to a display unit.

Upon powering of imager 100, it is in standby mode and page 410 is shown as depicted in FIG. 8 in accordance with one embodiment of the present invention. Display 400 is shown as page 410 providing a plurality of fields. The fields depicted include fields grouped to display surgical information 600, multimedia status 610, image panel 620, and control panel 630. In the embodiment illustrated, multimedia status 610 indicates that the optical media includes data saved from a previous surgical session. To use imager 100 for the current session and input patient data, user 10 touches the desired field in surgical information block 600 to include the requisite data.

Figure 9:
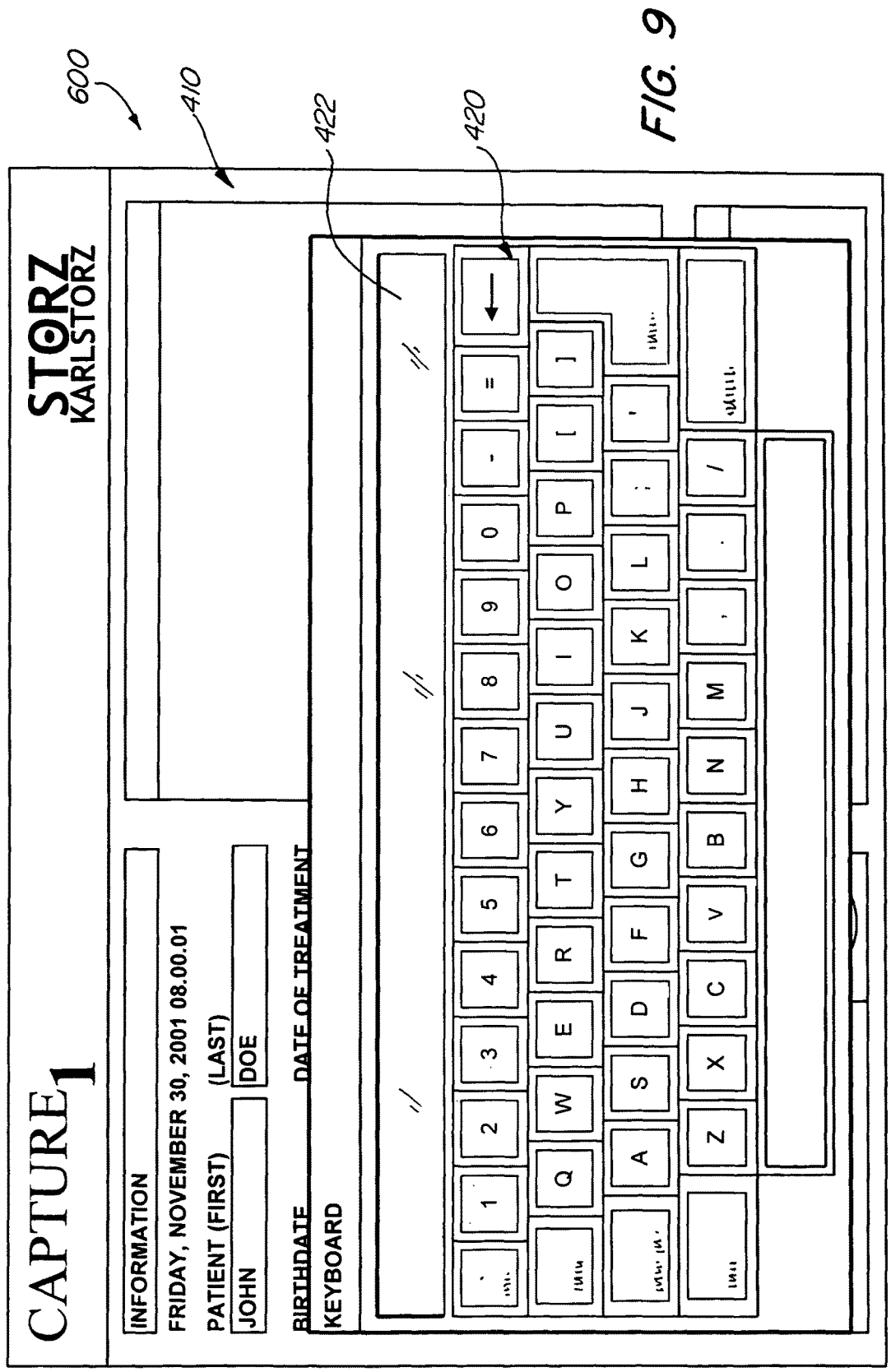
Figure 10:
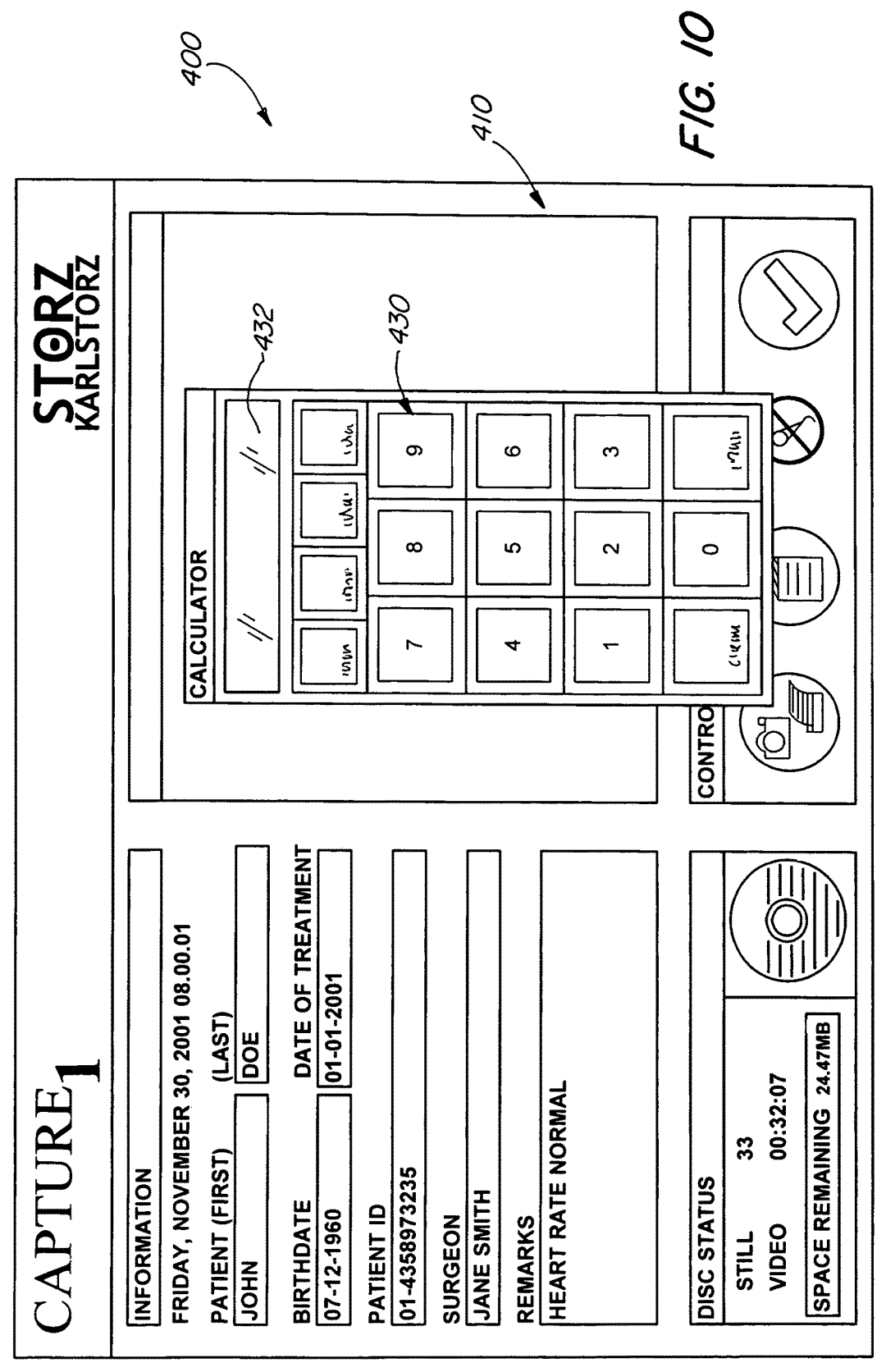

Surgical information block 600 includes fields for biographical patient information, identity of treating physician, and additional information as may be convenient and necessary. If the field requires an alpha-numeric entry, alpha-numeric keyboard page 420 is displayed on top of page 410, as depicted in FIG. 9. User 10 enters the data by touch. Field 422 contemporaneously displays the entry made. The user confirms the entry and is taken back to page 410 to make the next selection. If the desired field of frame 410 requires a numeric entry, numeric keyboard page 430 is displayed on top of page 410, as depicted in FIG. 10 according to one embodiment of the present invention. User 10 enters the data by touch. Field 422 contemporaneously displays the entry made. The user confirms the entry and is taken back to page 410, now modified with additional date as depicted in FIG. 11 according to one embodiment of the present invention, to make the next selection.

Returning to FIG. 8, control panel 630 provides functions to control imager 100 including recording video, capturing images, muting audio input, and confirming choices. Other functions as may be convenient and/or necessary may also be included.

Figure 12:
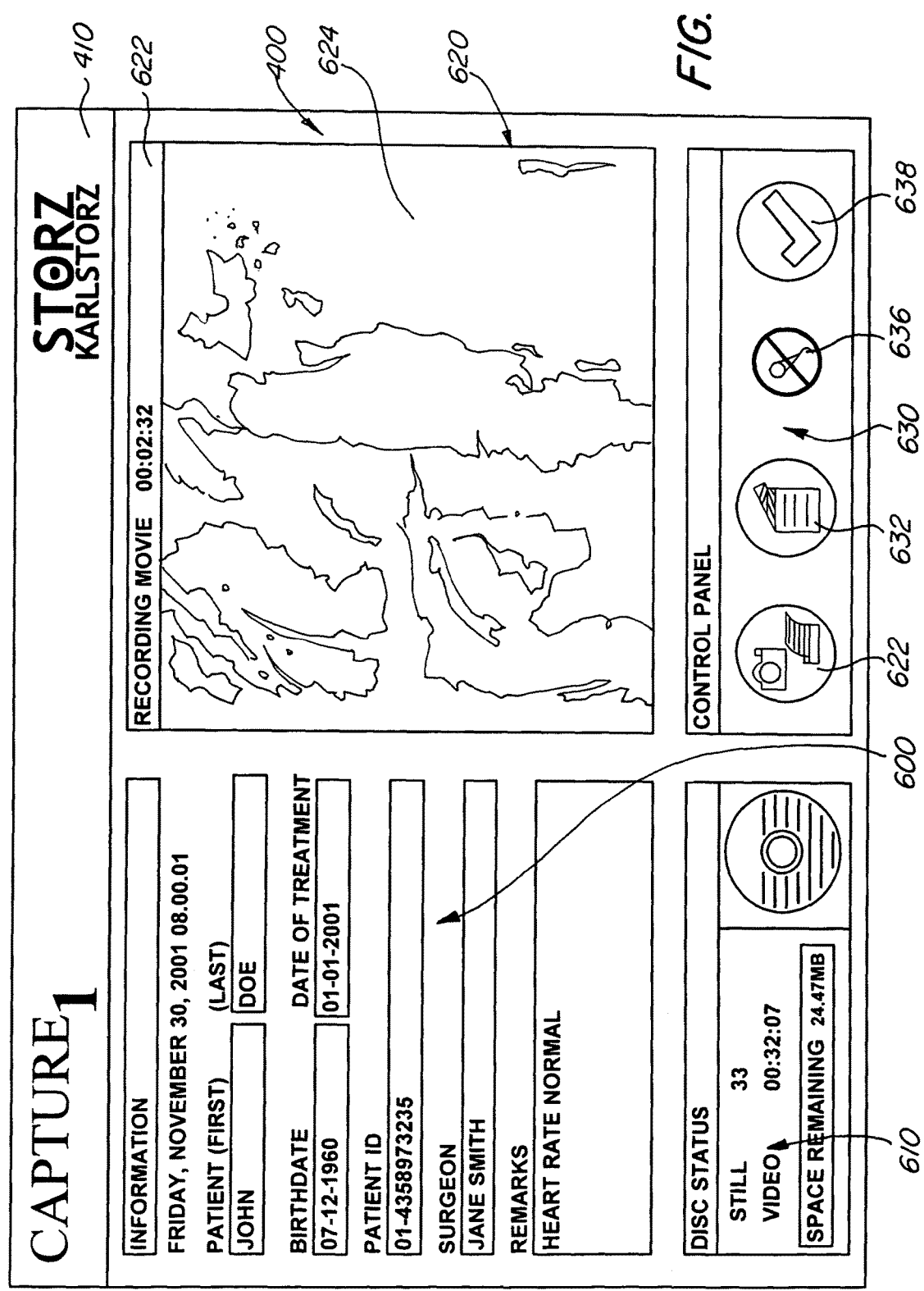

To place device in recording mode to record a video file to a disk properly loaded in OMD 125, user 10 touches the designated icon, here illustrated as icon 632, in control panel icon 630. In response, icon 632 may change design, such as becoming highlighted. Concurrently, in image panel 620, image 25 is displayed in image window 624 and image status bar 622 displays confirmation of recording and elapsed recording as depicted in FIG. 12. Similarly if recording is initiated via CCU 30, icon 632 becomes highlighted, image 25 is displayed in image window 624 and image status bar 622 displays confirmation of recording and elapsed recording, also as depicted in FIG. 12 according to one embodiment of the present invention. To cease recording, user 10 touches highlighted icon 632 or engages the appropriate control on CCU 30.

To mute audio recording or conversely engage audio recording, user 10 touches the designated icon, here illustrated as icon 636, in control panel 630. In response, icon 636 may change design, such as becoming highlighted. To reverse the action, user 10 touches icon 636 which in response may change design, preferably returning to its previous design.

To capture an image that is being displayed in image window 624, user 10 touches the designated icon, here illustrated as icon 634, in control panel 630 and imager 100 is placed in image capture mode and the instruction is processed as described above. In response, icon 634 may change design, such as becoming highlighted, and a confirmation message that the desired action is being performed will be displayed. Similarly, image capture mode can be accessed if user 10 engages the appropriate control on CCU 30 to capture image 26 that is being displayed in image window 624. Instruction is processed as described above and icon 634 may change design, such as becoming highlighted, and a confirmation message that the desired action is being performed will be displayed.

To allow user 10 to monitor available resources on a multimedia disc, multimedia status 610 includes fields identifying the remaining capacity of disc and the number of images captured and the length of time of image stream 25 recorded.

The archival mode is accessible from control panel 630 to review and/or manipulate saved documentary recording files and graphics file. User 10 touches the designated icon, here illustrated as icon 638, and review page 440 is displayed as depicted in FIG. 13 according to one embodiment of the present invention. Page 440 preferably includes a control panel 630*a*, note area 670, file directory 660, image panel 620 including image window 624, image status bar 622, and controls 626. Controls 626 preferably include pause, playback, print and confirmation means as well as elapsed time and other controls as deemed useful and/or necessary.

Therein, a graphic file may be printed to printer 45 located in the surgical suite so that it is immediately available for review by user 10. Software is provided to enlarge and view and manipulate the graphic file such as providing visual contrast, inserting a scaled file object corresponding to a physical prosthesis and thus determining whether such prosthesis fits patient 5.

In accordance with one embodiment of the present invention, sensor 318 (see FIG. 4) is provided for detecting an infrared remote control signal. Sensor 318 enables user 10 to remotely operate imager 100. Sensor 318 is in communication with the processor or Microprocessor main board (MMB) 115, the sensor receiving control signals to operate the medical instrument.

In accordance with one embodiment of the present invention, a system for speech recognition is provided for user 10 interaction with imager 100. Microphone 40 receives user 10 voice commands, which are routed to speech recognition module 319. Speech recognition module 319 is software that executes on Microprocessor main board (MMB) 115 to receive voice signals that control the medical instrument.

In accordance with one embodiment of the present invention, database module 321 provides a database server and/or database management application that is operatively provided to enable user 10 to access, manage and/or update data in imager 100. Database module 321 is software that executes on Microprocessor main board (MMB) 115 to establish control signals to operate the hard drive and the optical media drive.

In accordance with one embodiment of the present invention, expert system 323 is provided wherein characteristics of video signal 300 meeting predetermined characteristics are automatically brought to the attention of user 10 and/or saved as graphic files 810. Expert system 323 is software that executes on Microprocessor main board (MMB) 115 to generate control signals to operate the medical instrument.

In accordance with one embodiment of the invention, a stereoscopic module 324 is provided for associating a plurality of video signals 300 with each other, as such providing stereoscopic images on a display unit. Stereoscopic module 324 is software that executes on Microprocessor main board (MMB) 115 to associate a plurality of files to provide stereoscopic images on a multimedia interface.

What is claimed is:

1. A medical video instrument having touch screen control comprising:
    a touch screen for entering control commands to control said medical video instrument;
    said medical video instrument for inserting into a body cavity and generating an image stream representative of the body cavity and displayed on said touch screen;
    a processor coupled to said touch screen and the medical video instrument such that said processor receives said control commands from said touch screen and generates control signals to operate said medical video instrument, said processor further provided for receiving the image stream; and
    a medical instrument housing enclosing said processor, said touch screen movable between a first position at least partially within a footprint of said medical instrument housing and a second position extended from said footprint of said medical instrument housing, said touch screen deflectable about an axis of said medical instrument housing wherein said touch screen is unpluggable from said medical instrument housing such that said touch screen may be disconnected from said medical instrument housing.

2. The medical instrument of claim 1 in which said medical instrument housing includes a stackable mating plug portion.

3. The medical instrument of claim 2 in which said touch screen includes a stackable mating plug portion.

4. The medical instrument of claim 1 in which said touch screen can be used by a plurality of medical instruments.

5. The medical video instrument according to claim 1 wherein said medical video instrument generates video data that is displayed on said touch screen.

6. The medical video instrument according to claim 1 wherein said medical video instrument further comprises a storage for storing the image stream.

7. The medical video instrument according to claim 1 wherein when said touch screen is in the first position, said touch screen is positioned within an interior cavity of said medical instrument housing and when said touch screen is moved to the second position, the touch screen positioned at least partially outside of said cavity.

8. A medical video instrument having touch screen control comprising:
    a touch screen for entering control commands to control said medical video instrument;
    said medical video instrument for inserting into a body cavity and generating an image stream representative of the body cavity and displayed on said touch screen;
    a processor coupled to said touch screen and the medical video instrument such that said processor receives said control commands from said touch screen and generates control signals to operate said medical video instrument, said processor further provided for receiving the image stream; and
    a medical instrument housing enclosing said processor, said touch screen movable between a first position at least partially within a footprint of said medical instrument housing and a second position extended from said footprint of said medical instrument housing, said touch screen deflectable about an axis of said medical instrument housing which said touch screen is easier to deflect in one direction than in the other direction.

9. The medical instrument of claim 1 in which said touch screen is more difficult to deflect in the opening direction than in the closing direction.

10. The medical instrument of claim 1 in which said touch screen presents a keyboard to a user.

11. The medical instrument of claim 1 further comprising a sensor in communication with said processor, said sensor receiving control signals to operate said medical instrument.

12. The medical instrument of claim 1 further comprising a speech recognition module executing on said processor, said speech recognition module receiving voice signals that control said medical instrument.

13. The medical instrument of claim 1 further comprising a expert system executing on said processor, said expert system generating control signals to operate said medical instrument.

14. The medical instrument of claim 1 in which said touch screen slides out of said medical instrument housing.

15. The medical instrument of claim 1 in which said touch screen slides out of said medical instrument housing and is deflectable.

16. A medical video instrument having touch screen control comprising:
- a touch screen for entering control commands to control said medical video instrument;
- said medical video instrument for inserting into a body cavity and generating an image stream representative of the body cavity and displayed on said touch screen;
- a processor coupled to said touch screen and the medical video instrument such that said processor receives said control commands from said touch screen and generates control signals to operate said medical video instrument, said processor further provided for receiving the image stream; and
- a medical instrument housing enclosing said processor, said touch screen movable between a first position at least partially within a footprint of said medical instrument housing and a second position extended from said footprint of said medical instrument housing, said touch screen deflectable about an axis of said medical instrument housing;
- wherein said touch screen is unpluggable from said medical instrument housing such that said touch screen may be disconnected from said medical instrument housing.

17. The medical instrument of claim 16 in which said medical instrument housing includes a stackable mating plug portion.

18. The medical instrument of claim 17 in which said touch screen includes a stackable mating plug portion.

* * * * *